US00PP15013P3

(12) United States Plant Patent
Bessho

(10) Patent No.: US PP15,013 P2
(45) Date of Patent: Jul. 13, 2004

(54) PETUNIA PLANT NAMED 'KAKEGAWA S66'

(50) Latin Name: *Petunia hybrida*
Varietal Denomination: Kakegawa S66

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 4 days.

(21) Appl. No.: 10/243,993

(22) Filed: Sep. 13, 2002

(65) Prior Publication Data

US 2004/0055065 P1 Mar. 18, 2004

(51) Int. Cl.[7] ..... A01H 5/00
(52) U.S. Cl. ..... Plt./356
(58) Field of Search ..... Plt./356

*Primary Examiner*—Bruce R. Campell
*Assistant Examiner*—Louanne Krawczewicz Myers
(74) *Attorney, Agent, or Firm*—Jondle & Associates P.C.

(57) ABSTRACT

A Petunia cultivar particularly distinguished by its pale lavender flower color with purple streaking at the petal base.

1 Drawing Sheet

Genus and species: *Petunia hybrida.*
Variety denomination: 'Kakegawa S66'.

BACKGROUND OF THE NEW PLANT

The present invention comprises a new and distinct cultivar of Petunia, botanically known as *Petunia hybrida*, and hereinafter referred to by the cultivar name 'Kakegawa S66'. 'Kakegawa S66' originated from a hybridization made in 1997 in Kakegawa, Japan. The male parent, 6B-1A-2, (unpatented) was a phenotypically fixed $F_3$ selection from a cross made in 1994 between two breeding lines named 4UK-1 and P-1a. The female parent of 'Kakegawa S66' was an $F_5$ selection known as 89S-829-1a-1a-1a-1, originating from a dwarf multiflora breeding gene pool. $F_1$ seed was obtained from this cross in 1997.

Two hundred $F_1$ plants from the 1997 cross were transplanted to the field in Salinas, Calif. during the summer of 1998. Seven plants were selected for further evaluation and vegetatively propagated. The seven plants were propagated again in 1999 and evaluated for trueness to type and ease of propagation. Final selection of one plant was made in Salinas, Calif. during the summer of 1999. 'Kakegawa S66' reproduces true to type in successive generations of aexual propagation.

'Kakegawa S66' has been found to retain its distinctive characteristics after three years and five cycles of vegetative propagation and this novelty is firmly fixed. The variety has demonstrated stability during this time and has no inherent variation or off-types.

DESCRIPTION OF PHOTOGRAPH

This new Petunia plant is illustrated by the accompanying photograph which show blooms, and foliage of the plant in full color, the colors shown being as true as can be reasonably obtained by conventional photographic procedures.

DESCRIPTION OF THE NEW CULTIVAR

Figure 1:
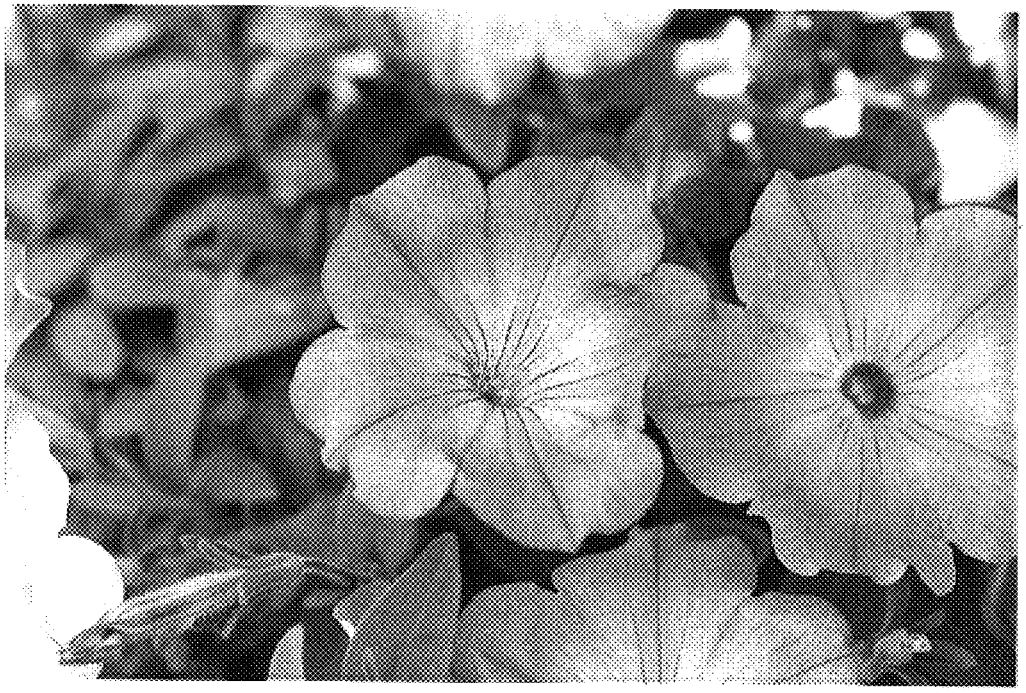
FIG. 1 shows the mature flower.
Figure 2:
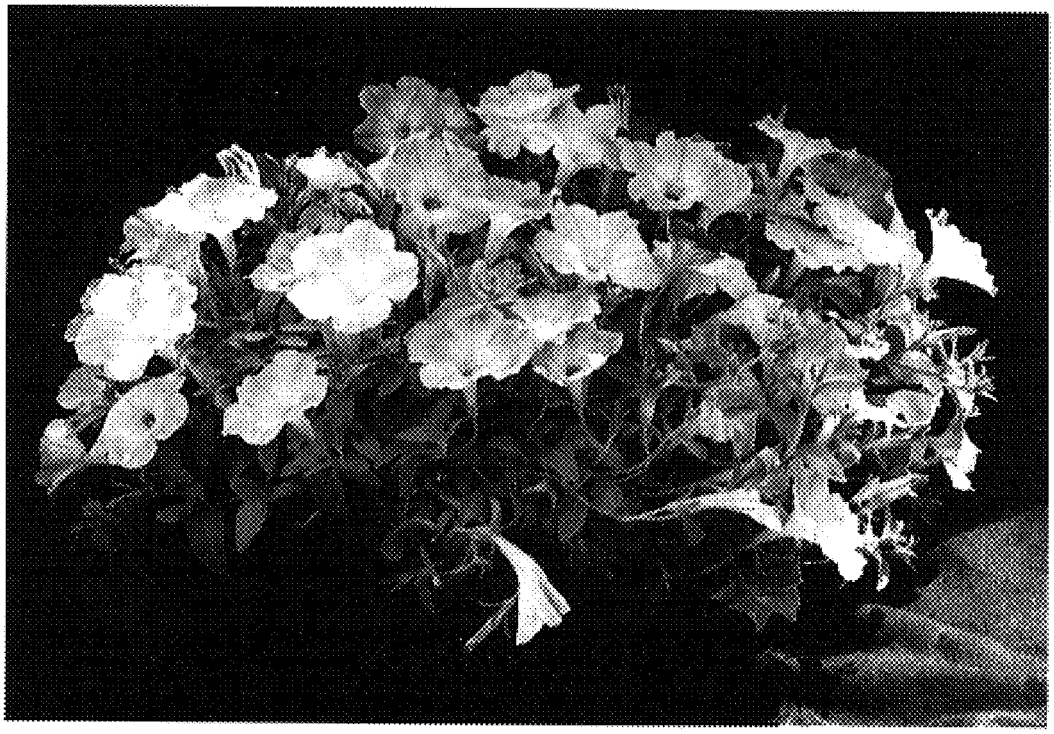
FIG. 2 shows the entire plant approximately twelve weeks after transplanting a rooted cutting in a six-inch pot.

The following detailed descriptions set forth the distinctive characteristics of 'Kakegawa S66'. The data which defines these characteristics were collected from asexual reproductions carried out in Salinas, Calif. Data was collected on plants in 15 cm diameter pots about twelve weeks after rooted cuttings were transplanted. Color references are primarily to The R.H.S. Colour Chart of The Royal Horticultural Society of London (R.H.S.).

DESCRIPTION OF THE NEW PLANT

Classification:
*Botanical.*—*Petunia hybrida.*
*Commercial.*—Petunia.

Parentage:
*Female parent.*—Breeding line 89S-829-1a-1a-1a-1 (not patented).
*Male parent.*—6B-1A-2, an $F_3$ selection from cross of breeding lines 4UK-1 and P-1a (not patented).

Environmental Conditions for Plant Growth

Plants were propagated from vegetative cuttings, and grown individually in 15 cm diameter plastic pots in a glass greenhouse located in Salinas, Calif. Pots contained a peat moss-based growing medium. Soluble fertilizer containing 18% nitrogen, 8% phosphorus and 18% potassium was applied in four, daily irrigations. The fifth irrigation was made with non-fertilized water. Pots were top-dressed with a slow release fertilizer containing 18% nitrogen, 8% phosphorus and 18% potassium. The typical average air temperature was 24C.

Growth:
*Habit.*—Branching, mounding.
*Form.*—Descending.
*Plant size.*—91 cm total diameter and 76 cm total height when three plants are grown in a 50 cm diameter hanging basket for 7–8 weeks.
*Flowering habit.*—Indeterminate throughout the growing season.

*Time to bloom from propagation.*—4–6 weeks after rooting when grown in 10–15 cm diameter plastic pots.
*Life cycle.*—Annual.

Stems:
*Color.*—Yellow-green (RHS 145A).
*Description.*—Round, pubescent.
*Diameter.*—2 to 3 mm.
*Internode length.*—4.0 cm.
*Stem length* (*main*).—76–92 cm when grown in a 64 cm diameter hanging basket and at full pot maturity.
*Stem length* (*lateral*).—38–46 cm when grown in a 64 cm diameter hanging basket and at full pot maturity.

Leaves:
*Arrangement.*—Opposite.
*Apex.*—Mucronate.
*Base.*—Oblique.
*Color.*—Upper surface is green (RHS 137B) and lower surface is green (RHS 138B).
*Margin.*—Entire.
*Size.*—Length is 4.8 cm at full expansion and width is 2.5 cm at full extension.
*Shape.*—Ovate.
*Texture.*—Coarse.
*Venation.*—Pinnate.
*Pubescence.*—Present, clear.
*Petiole length.*—1–3 mm.
*Petiole diameter.*—1–2 mm.
*Petiole color.*—Yellow-green (RHS 145A).

Flowers:
*Bud color.*—Yellow-green (RHS 149B).
*Bud shape.*—Ovate.
*Bud surface.*—Extensively pubescent.
*Bud length.*—1.3–1.6 cm.
*Bud diameter.*—0.4–0.6 cm.
*Calyx.*—5 sepals; 2 cm×8 mm (length×width); individual arising; not united nor fused.
*Sepal shape.*—Oblong.
*Sepal length.*—1.3–1.8 cm.
*Sepal width.*—0.3–0.4 cm.
*Sepal apex.*—Tapered.
*Sepal base.*—Decurrent.
*Sepal margin.*—Entire.
*Sepal color upper.*—Yellow-green (RHS 146A).
*Sepal color lower.*—Yellow-green (RHS 146A).
*Corolla.*—5 petals, fused.
*Flower width.*—6.0–6.5 cm.
*Flower depth.*—5.0–5.5 cm.
*Fragrant.*—Yes.
*Inflorescence type.*—Solitary.
*Pistil.*—One, compound.
*Ovary.*—Superior, parietal placentation.
*Stamens.*—5 total with two long and three short; white (RHS 155C).
*Anther.*—5 (2 long, 3 short).
*Filament length.*—8 mm (long); 5 mm (short).
*Filament color.*—White (RHS 155C).
*Style length.*—22–23 mm.
*Style color.*—Green (RHS 142C).
*Stigma color.*—Green (RHS 143B.
*Peduncle.*—1.5 cm×1 mm (length×width); pubescent; yellow-green (RHS 143B).
*Flower form.*—Radial symmetry.
*Flower habit.*—Erect.
*Flower number* (*per lateral stem*).—3 to 5.
*Flowering season.*—All year as long as the temperature is greater than 50 degrees F.
*Lastingness of bloom.*—4 to 5 days.
*Flower number of petals.*—5.
*Petal shape.*—Fused at base and lobed at tip.
*Flower petals fused at base.*—Yes.
*Petal length.*—5.7–6.3 cm.
*Petal width.*—2.7–3.2 cm.
*Petal apex.*—Truncate.
*Petal margin.*—Entire.
*Petal color.*—Lobes: upper — purple (RHS 77B); lower — purple (RHS 76B) with yellow-green (RHS 145B) veins. Tube — Inner — green (RHS 144D) with purple (RHS 77A) veins; Outside is yellow-green (RHS 144B) with green (RHS 140A) veins.
*Petal pubescence.*—Absent.
*Corolla tube diameter.*—7 mm.
*Corolla tube length.*—2.5–3.0 cm.
*Pollen amount* (*relative*).—Profuse.
*Pollen color.*—White (RHS 155C).
*Produces seed.*—Yes.

Disease and Insect Resistance

No susceptibility to diseases or insects noted to date.

Comparison with Known Cultivars

'Kakegawa S66' is a distinct variety of petunia owing to its pale lavender flower color and purple streaking at the petal base. 'Kakegawa S66' is most similar to the variety 'Cascadia Charme' (U.S. Plant Pat. No. 8,934) however there are numerous differences as shown in the table below.

| Characteristics | 'Kakegawa S66' | 'Cascadia Charme' |
|---|---|---|
| Petal Shape | Rounded | Pointed |
| Inner Corolla Tube Vein Color | Purple(RHS 77A) | Yellow-green(RHS 145B) |
| Flower Diameter | 6.0–6.5 cm | 7.0–8.5 cm |
| Leaf Width | 2.5 cm | 5.5 cm |
| Leaf Length | 4.8 cm | 7.0–8.5 cm |

Comparison with Parental Cultivars

| Characteristics | 'Kakegawa S66' | Female 89S-829-1a-1a-1a-1 | Male 6B-1A-2 |
|---|---|---|---|
| Plant habit | Mounding and branching | Dwarf and compact | Creeping |
| Flower size | Grandiflora | Multiflora | Grandiflora |
| Flower petal color | Lt. pink | Pink | Pale pink |

I claim:

1. A new and distinct cultivar of Petunia plant named 'Kakegawa S66' as described and illustrated herein.

* * * * *